(12) United States Patent
Ocvirk et al.

(10) Patent No.: US 9,220,451 B2
(45) Date of Patent: Dec. 29, 2015

(54) METHOD AND FUEL CELL FOR ELECTROCHEMICAL MEASUREMENT OF ANALYTE CONCENTRATION IN VIVO

(75) Inventors: Gregor Ocvirk, Nierstein (DE); Karl-Heinz Kölker, Grünstadt (DE)

(73) Assignee: Roche Diabetes Care, Inc., Indianapolis, IN (US)

( * ) Notice: Subject to any disclaimer, the term of this patent is extended or adjusted under 35 U.S.C. 154(b) by 45 days.

(21) Appl. No.: 13/608,618

(22) Filed: Sep. 10, 2012

(65) Prior Publication Data

US 2013/0253293 A1 Sep. 26, 2013

Related U.S. Application Data

(63) Continuation of application No. PCT/EP2010/006770, filed on Nov. 6, 2010.

(30) Foreign Application Priority Data

Mar. 11, 2010 (EP) .................................. 10002588

(51) Int. Cl.
*A61B 5/1486* (2006.01)
*A61B 5/145* (2006.01)
(Continued)

(52) U.S. Cl.
CPC ........... *A61B 5/1486* (2013.01); *A61B 5/14532* (2013.01); *C12Q 1/001* (2013.01); *H01M 8/16* (2013.01); *Y02E 60/527* (2013.01)

(58) Field of Classification Search
CPC .. A61B 5/1468; A61B 5/1486; A61B 5/1473; A61B 5/1482; A61B 5/14735; A61B 5/14865; A61B 5/14532; Y02E 60/50; Y02E 60/52; Y02E 60/521; Y02E 60/522; Y02E 60/523; Y02E 60/525; Y02E 60/526; Y02E 60/527; Y02E 60/528; Y02E 60/56; Y02E 60/563; Y02E 60/566
USPC ................................ 600/309, 345, 347, 365; 204/403.01–403.15; 436/63
See application file for complete search history.

(56) References Cited

U.S. PATENT DOCUMENTS 3,837,339 A 9/1974 Aisenberg et al.
4,600,602 A * 7/1986 Martin et al. ................. 427/98.4
(Continued)

FOREIGN PATENT DOCUMENTS

CN 101351913 A 1/2009
EP 0 300 082 A2 1/1989
(Continued)

OTHER PUBLICATIONS

Yamazaki et al. "A Fuel Cell with Selective Electrocatalysts using Hydrogen Peroxide as both an Electron Acceptor and a Fuel." Journal of Power Sources 178 (2008) 20-25. Available online Dec. 15, 2007.*
(Continued)

*Primary Examiner* — Navin Natnithithadha
*Assistant Examiner* — Meredith Weare
(74) *Attorney, Agent, or Firm* — Bose McKinney & Evans LLP

(57) ABSTRACT

The invention relates to a method for the electrochemical measurement of an analyte concentration in vivo, comprising a fuel cell with which the analyte to be measured is reacted catalytically with an enzyme contained in an enzyme layer and which supplies an electrical voltage, dependent on the analyte concentration to be measured, beween an anode and a cathode, which voltage is measured. In the catalytic reaction of the analyte to be measured in the enzyme layer, a product is generated which, as fuel of the fuel cell, oxidizes on the anode and is reduced on the cathode. The invention further relates to a fuel cell for such a method.

10 Claims, 4 Drawing Sheets

(51) Int. Cl.
*H01M 8/16* (2006.01)
*C12Q 1/00* (2006.01)

(56) References Cited

U.S. PATENT DOCUMENTS

| | | | |
|---|---|---|---|
| 6,294,281 B1* | 9/2001 | Heller | 429/401 |
| 7,018,518 B2 | 3/2006 | Willner et al. | |
| 7,081,683 B2 | 7/2006 | Ariav | |
| 8,415,059 B2* | 4/2013 | Minteer et al. | 429/401 |
| 2004/0074785 A1* | 4/2004 | Holker et al. | 205/777.5 |
| 2004/0245101 A1* | 12/2004 | Willner et al. | 204/403.01 |
| 2005/0118494 A1 | 6/2005 | Choi | |
| 2005/0242479 A1* | 11/2005 | Petisce et al. | 264/650 |
| 2005/0279646 A1* | 12/2005 | Hasegawa et al. | 205/789 |
| 2006/0154126 A1 | 7/2006 | Ritts et al. | |
| 2007/0007133 A1* | 1/2007 | Mang et al. | 204/403.14 |
| 2007/0181418 A1* | 8/2007 | Hasegawa et al. | 204/194 |
| 2008/0026473 A1* | 1/2008 | Wang et al. | 436/63 |
| 2008/0118782 A1 | 5/2008 | Heller et al. | |
| 2008/0160384 A1 | 7/2008 | Iqbal et al. | |
| 2010/0213057 A1* | 8/2010 | Feldman et al. | 204/403.14 |
| 2011/0014549 A9* | 1/2011 | Minteer et al. | 429/523 |
| 2011/0196216 A1* | 8/2011 | Quarder et al. | 600/345 |

FOREIGN PATENT DOCUMENTS

| | | | |
|---|---|---|---|
| WO | WO 97/19344 A1 | 5/1997 | |
| WO | WO 00/22688 A2 | 4/2000 | |
| WO | WO 03/019170 A1 | 3/2003 | |
| WO | WO 2007/084249 A2 | 7/2007 | |

OTHER PUBLICATIONS

McDowall, Jennifer. "Glucose Oxidase and Biosensors." May 2006. http://www.ebi.ac.uk/interpro/potm/2006_5/Page1.htm.*
Odebunmi et al. "Kinetic and Thermodynamic Studies of Glucose Oxidase Catalysed Oxidation Reaction of Glucose." Journal of Applied Sciences and Environmental Management, vol. 11, No. 4, 2007, pp. 95-100.*
Goodsell, David. "Glucose Oxidase." May 2006. 3 pages. http://www.rcsb.org/pdb/101/motm.do?momID=77.*
International Preliminary Report on Patentability; PCT/EP2010/006770; Sep. 25, 2012.
International Search Report; PCT/EP2010/006770; Feb. 18, 2011.
Pizzariello et al., A glucose/hydrogen peroxide biofuel cell that uses oxidase and peroxidase as catalysts by composite bulk-modified bioelectrodes based on a solid binding matrix, Bioelectrochemistry 56, Amsterdam, Netherlands (2002) 99-105.

* cited by examiner

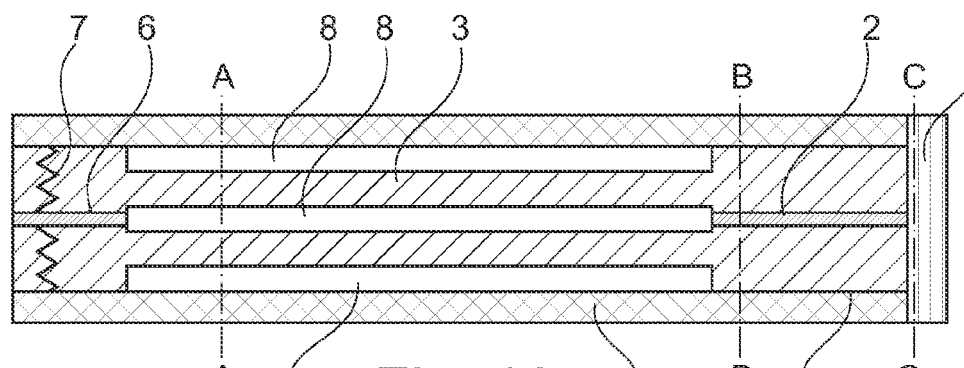
Fig. 12
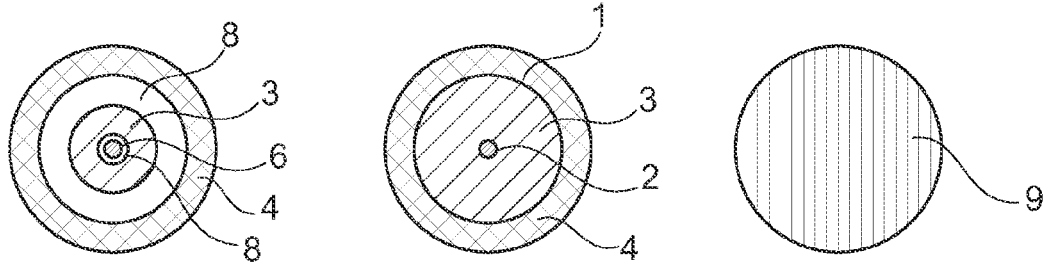
Fig. 13  Fig. 14  Fig. 15
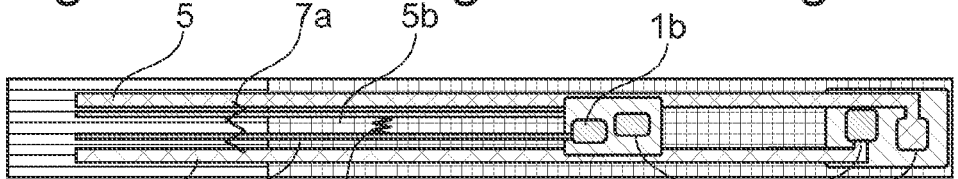
Fig. 16
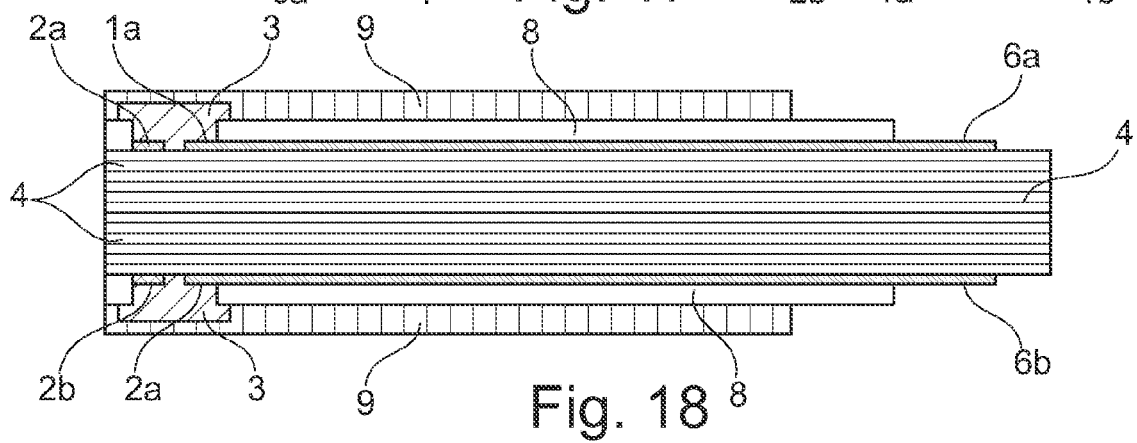
Fig. 17
Fig. 18

METHOD AND FUEL CELL FOR ELECTROCHEMICAL MEASUREMENT OF ANALYTE CONCENTRATION IN VIVO

RELATED APPLICATIONS

This application is a continuation of PCT/EP2010/006770, filed Nov. 6, 2010, which claims priority to EP10002588.1, filed Mar. 11, 2010, both of which are incorporated herein by reference in their entirety.

BACKGROUND

The invention relates to a method for the electrochemical measurement of an analyte concentration in vivo by means of a fuel cell which catalytically converts the analyte to be measured with an enzyme contained in an enzyme layer and supplies an electrical voltage between an anode and a cathode.

As is known from U.S. Pat. No. 3,837,339, fuel cells are used as electrochemical sensors for in vivo measurement of analyte concentrations, for example, glucose concentration. Therein, the analyte to be measured is catalytically converted as the fuel of the fuel cell. The fuel cell described in U.S. Pat. No. 3,837,339 oxidizes glucose on the anode, thereby generating gluconic acid. Oxygen is reduced on the cathode.

In order to improve the efficiency of these reactions, it is known to provide the cathode with an enzyme layer which contains an enzyme for catalytically converting the analyte and to apply an enzyme layer containing an enzyme to the anode for the catalytic reduction of oxygen. For example, such fuel cells are known from U.S. Publication No. 2005/0118494. In these fuel cells, the anode is covered with an enzyme layer which contains glucose oxidase and the cathode is covered with an enzyme layer which contains laccase. In this manner, the anode reaction, i.e. the oxidation of glucose, and the cathode reaction, i.e. the reduction of oxygen, can be accelerated.

A problem arising in connection with the in vivo measurement of analyte concentrations with such sensors is that the intensity of the measuring signal can be affected by an oxygen deficiency in the environment of the cathode. In particular in the event of prolonged operation, depletion of the oxygen concentration can occur in the environment of the cathode, the oxygen concentration being already subject to great variations in subcutaneous fatty tissue. This may falsify the measuring signal. A further problem is that intermediate products that are harmful to health or even toxic, for example, hydrogen peroxide, can often develop in the catalytic conversion of analytes. If such intermediate products exit from the sensor, this may result in inflammation and require premature removal of the sensor.

SUMMARY

The present invention provides a method of measuring analyte concentrations over a prolonged period of time in a cost-effective and precise manner.

In exemplary embodiments, a product is generated in the enzyme layer by catalytic conversion of the analyte to be measured, said product then oxidizing on the anode and being reduced on the cathode. In this manner, a measuring signal independent of the local oxygen concentration can be achieved because the oxygen reduction reaction on the cathode, which occurs in prior art devices, is no longer required. For this reason, the method according to these teachings allows measuring analyte concentrations in vivo with improved precision over a prolonged period of time.

With the method taught herein, it is, for example, possible to generate hydrogen peroxide as a product by catalytic conversion of the analyte to be measured, wherein said hydrogen peroxide subsequently oxidizes on the anode and can be reduced on the cathode. By converting the hydrogen peroxide, which is problematic in terms of health, both on the anode and on the cathode, the concentration thereof is, typically, only half as high as in conventional sensors which convert hydrogen peroxide only at one electrode. For this reason, harmful effects of the hydrogen peroxide can be avoided to a far better degree than is the case with conventional sensors. As an alternative to hydrogen peroxide, use can also be made of other redox amphoteric substances, such as sulfites and aldehydes. An example of a redox amphoteric aldehyde is 5-hydroxy indolyl acetaldehyde which can be generated from serotonin using monoamine oxidases and which oxidizes to 5-hydroxy indolyl acetic acid and can also be reduced to 5-hydroxytryptophol.

For the method according to this disclosure, an electrochemical sensor which comprises an anode and a cathode is used for in vivo measurement of an analyte concentration. The surface of the cathode is formed of a different material than that of the anode. The anode, the cathode and an enzyme layer which contains an enzyme for the catalytic conversion of the analyte to be measured form a fuel cell. The enzyme layer of the sensor forms a diffusion path for a product generated by catalytic conversion of the analyte, with the result that the sensor oxidizes this product on the anode and reduces it on the cathode.

A reaction competing with the reduction of the product generated by catalytic conversion of the analyte may be the reduction of oxygen. Practically, however, this competitive reaction can be disregarded because the reduction of the product generated by catalytic conversion of the analyte predominates. If the product is hydrogen peroxide, the reaction rate of the reduction of oxygen, typically, is less than a tenth, normally even less than a hundredth of the reaction rate of the reduction of hydrogen peroxide. In other words, more than 10, normally even more than 100 molecules of hydrogen peroxide are reduced for one molecule of oxygen. In a sensor according to these teachings, the product is, therefore, oxidized on the anode and reduced on the cathode as a signal determining reaction. This means that the signal contents of any competitive reactions are less than 10 percent of the signal intensity.

On the one hand, the fact that the oxygen reduction can be disregarded is based on an overpotential of oxygen. Such an overpotential always occurs in redox systems to a greater or lesser extent. The reduction reaction of oxygen is inhibited by this overpotential and, therefore, takes place at a rate that is significantly slower than the reduction of the product generated by catalytic conversion of the analyte. On the other hand, the standard electrode potential of oxygen, which is only 1.22 V, is relatively small, in particular in comparison with the standard electrode potential of hydrogen peroxide, which is 1.77 V. For this reason, the reduction of oxygen is thermodynamically disadvantageous in this respect as well.

A fuel cell according to this disclosure may not only be used as a sensor for the measurement of an analyte concentration but also as an energy source of an implanted device in the body of a patient, for example, for a cardiac pacemaker.

In a fuel cell according to this disclosure, the enzyme layer forms a diffusion path for the product generated by catalytic conversion of the substance or the analyte, with the result that this product oxidizes on the anode and is reduced on the cathode while the sensor is in use. This can be most easily achieved by the enzyme layer touching both the anode and the cathode. For example, the anode and the cathode can be arranged on a common substrate, wherein the enzyme layer covers both the anode and the cathode. A further possibility is to arrange the enzyme layer between the anode and the cathode. In particular in case of a sandwiched arrangement, further intermediate layers may be provided between the enzyme layer and the anode or between the enzyme layer and the cathode, provided these intermediate layers are permeable to the redox amphoteric product, for example, hydrogen peroxide.

Inasmuch as a sensor is mentioned in the following description, the features referred to therein can also be used in a fuel cell according to these teachings, which is used as an energy source of a cardiac pacemaker or another device in the body of a patient. In particular, a sensor as taught herein can be readily used as an energy source for a cardiac pacemaker.

The exemplary sensor can be produced in a very simple and cost effective manner because, in essence, the only items required are an anode, a cathode and the enzyme layer. The expenditure connected with the production of separate enzyme layers for anode and cathode can be avoided.

The enzyme molecules that are typically included in the enzyme layer are an oxidase, for example glucose oxidase or lactose oxidase, but can, for example, also be a hydrogenase. The enzyme molecules can be covalently bonded in the enzyme layer. It is, however, also possible that the enzyme molecules are only admixed to the material of the enzyme layer and are mobile in the enzyme layer. Particularly in this case, the enzyme layer can be covered with a top layer, for example, with a polymer film, which is impermeable to enzyme molecules. Suitable top layers which are permeable to water and the analyte molecules to be measured can, for example, be produced from polyurethanes, polyvinyl chlorides, polycarbonates, polytetrafluoroethylenes, acrylates or silicones. Sulfonated tetrafluoroethylenes, such as they are commercially available under the brand name of Nafion, are particularly suitable.

For the enzyme layer, use can, in particular, be made of polymers that are permeable to water. Particularly suitable are plastics, for example, polyurethane. Further possibilities are, for example, pectin, gelatin or other natural materials that are permeable to water. The enzyme layer can be formed as a plastic matrix with included enzyme molecules.

Ideally, the enzyme layer consists of a material that is an insulator in its dry state. For operation of the sensor, the enzyme layer takes up water and becomes a ionic conductor. It is desirable that the intermediate product has a high mobility inside the enzyme layer.

The cathode of the sensor according to these teachings can have a metallic surface, for example of palladium. However, other noble metals and noble metal alloys are also suitable. In this manner, the cathode can be cost effectively formed as a conducting track on a substrate of plastic. The cathode can also be designed with a non-metallic surface which allows a reduction of the intermediate product.

The anode can, likewise, have a metallic surface provided it consists of a different metal than that of the cathode surface. However, the anode typically has a non-metallic surface, for example a surface that contains carbon particles or graphite particles. The non-metallic surface of the anode can be arranged as a covering on a metallic conductor.

Carbon black or graphite particles can be easily mixed with a polymeric binding agent to form a paste into which catalytically active particles can be blended. Suitable blendings allow the generation of pastes of varying compositions, said pastes then serving to form the cathode and/or anode on metallic conducting tracks.

Preferably, a conductor running to the anode is connected to a conductor running to the cathode via an electrical resistor. This resistor causes a continuous electric current between the anode and the cathode, with the result that the redox amphoteric product is converted continuously, this being an important advantage in particular in case of products that are problematic in terms of health, such as hydrogen peroxide.

A further advantage is that, in contrast to conventional amperometric hydrogen peroxide sensors, no external voltage supply is required in order to continuously convert hydrogen peroxide.

The electrical resistor can, for example, be formed as a conducting track on a substrate on which there is also the conductor running to the anode and the conductor running to the cathode. The conducting track used for forming the resistor can be made of the same material as that of the conducting tracks running to the anode and the cathode, wherein their diameter, in particular their thickness and/or their width, is selected appropriately small in order to obtain the desired value of the resistor. However, the resistor can be made of a different material than that of the conductors running to the anode and the cathode. For example, a conducting track can be made as a paste of a resistor material and printed onto the substrate. The resistor also can be a material mixture which contains carbon particles, for example carbon black and/or graphite, and a binding agent. For example, a paste that contains carbon particles and solidifies after having been applied can be a suitable resistor material. The resistor typically has a value of at least 1 megohm. As a general rule, however, resistance values in excess of 1 gigaohm are not advantageous. As a general rule, resistance values between 10 megohms and 100 megohms are advantageous.

The electrical resistor can, however, also be integrated into a plug contact which is connected to both conducting track ends in a conducting manner during operation of the sensor.

An advantageous refinement provides that both the reduction and the oxidation of the redox amphoteric product which is generated by enzymatic conversion of the analyte to be measured are supported by electrochemically active catalysts. Catalysts that are suitable for the oxidation of hydrogen peroxide are, for example, metal oxides, in particular manganese dioxide, and metallo-organic compounds, for example cobalt phthalocyanine. In particular, manganese dioxide in powder form can be easily mixed with graphite particles and, in this manner, be integrated into the surface of the anode.

BRIEF DESCRIPTION OF THE DRAWINGS

Further details and advantages of this disclosure will be illustrated by means of embodiments with reference being made to the accompanying drawings. Therein, identical parts or parts that are corresponding to each other are designated with consistent reference symbols.

FIG. 12 is a longitudinal sectional view of a further embodiment of a sensor according to the invention;

FIG. 13 is a sectional view taken from cutting line AA of FIG. 12;

FIG. 14 is a sectional view taken from cutting line BB of FIG. 12;

FIG. 15 is a sectional view taken from cutting line CC of FIG. 12;

FIG. 16 shows a further exemplary embodiment of a sensor according to the invention;

FIG. 17 is a sectional view of FIG. 16; and

FIG. 18 shows a further embodiment of a sensor according to the invention.

DETAILED DESCRIPTION

The embodiments described below are not intended to be exhaustive or to limit the invention to the precise forms disclosed in the following detailed description. Rather, the embodiments are chosen and described so that others skilled in the art may appreciate and understand the principles and practices of this disclosure.

Figure 1:
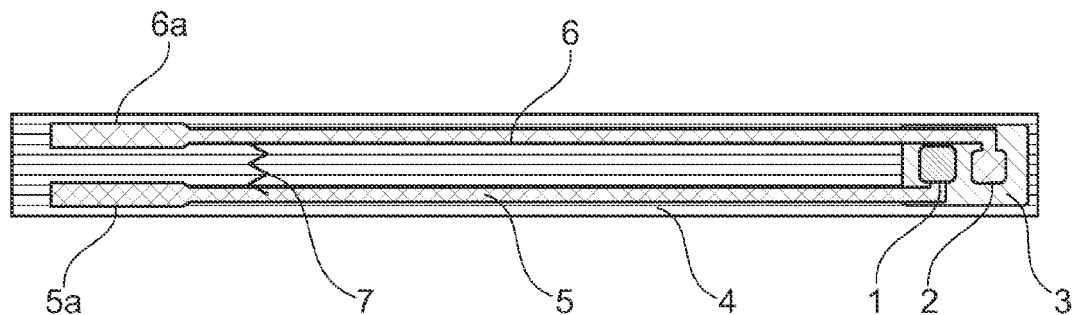
FIG. 1 shows an embodiment of a sensor according to the invention.

The sensor shown in FIG. 1 works according to the principle of a fuel cell. A redox amphoteric product which forms the fuel of the fuel cell is generated from the analyte to be measured, for example glucose or lactate. For this reason, the energy supplied by the fuel cell becomes higher as the analyte concentration to be measured increases. The electrical voltage drop across a load resistor between the anode and the cathode can, therefore, be used as a measuring signal for determining the analyte concentration.

Figure 2:
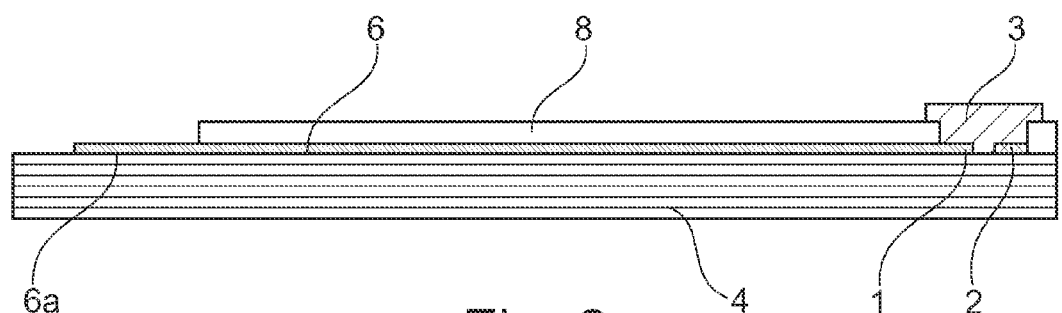
FIG. 2 is a sectional view of FIG. 1.

The sensor shown in a top view in FIG. 1 and in a sectional view in FIG. 2 has an anode 1 and a cathode 2 which are covered by a common enzyme layer 3. The anode 1 and the cathode 2 are each disposed at the end of a conducting track 5, 6 arranged on a substrate 4, for example a plastic sheet. The conducting tracks 5, 6 can consist of a noble metal, for example palladium, which may also form the surface of the cathode 2. The anode 1 can be formed as a covering of the conducting track 5, for example made of carbon particles and a binding agent. The two conducting tracks 5, 6 are connected to an electrical load resistor 7 and are covered by an electrically insulating layer 8 that is impermeable to water. The ends of the conducting tracks 5, 6 project from under the insulating layer 8. Hence, the contact surfaces 5a, 6a are not covered by the electrically insulating layer 8 that is impermeable to water, just as is the case with the anode 1 and the cathode 2.

The analyte molecules, for example glucose molecules, that are diffusing into the enzyme layer 3 that is permeable to water are enzymatically converted by the enzyme molecules contained in the enzyme layer 3, for example an oxidase, whereby a redox amphoteric product, for example hydrogen peroxide, is generated. The redox amphoteric product is mobile in the enzyme layer 3 and, therefore, arrives both at the anode 1 and the cathode 2. The redox amphoteric product is oxidized on the anode 1 and reduced on the cathode 2. In order to promote the oxidation reaction, a catalyst, for example manganese dioxide, can be admixed to the anode material. Since the redox amphoteric product is electrochemically converted on the anode 1 and on the cathode 2, an electrical voltage develops between the anode 1 and the cathode 2. The electrical voltage between the anode 1 and the cathode 2 is measured across the load resistor 7 and used as a measuring signal for determining the analyte concentration. The end 5a and 6a facing away from the anode 1 and the cathode 2 can be broadened in order to act as contact pads facilitating the connection of a voltage meter.

In an ideal fuel cell, the voltage between the anode 1 and the cathode 2 is only dependent on the electrochemical potentials which develop as a result of the anode and cathode reactions and on the size of the load resistor 7 between the anode 1 and the cathode 2. For this reason, the electrical voltage between the anode 1 and the cathode 2 across the load resistor 7 develops as a result of the reaction rates of the reaction on the anode 1 and the reaction on the cathode 2.

Since, in the sensor shown, the same substance, e.g., hydrogen peroxide, is converted at both the anode 1 and the cathode 2, both the anode reaction and the cathode reaction are, essentially, determined by the analyte concentration in the enzyme layer 3. That is to say, the rate at which the product is generated, which is converted at the anode 1 and the cathode 2, is approximately proportional to the analyte concentration within a wide concentration range.

The load resistor 7 can be formed by a conducting track of resistor material, for example a paste containing graphite particles, which connects the conducting track 5 running to the anode 1 to the conducting track 6 running to the cathode 2. Preferably, the resistor 7 is arranged below the insulating layer 8. In principle, however, it is also possible to use the resistor 7 to connect the connection-sided ends of the conducting tracks 5, 6 projecting from under the insulating layer 8.

Figure 3:
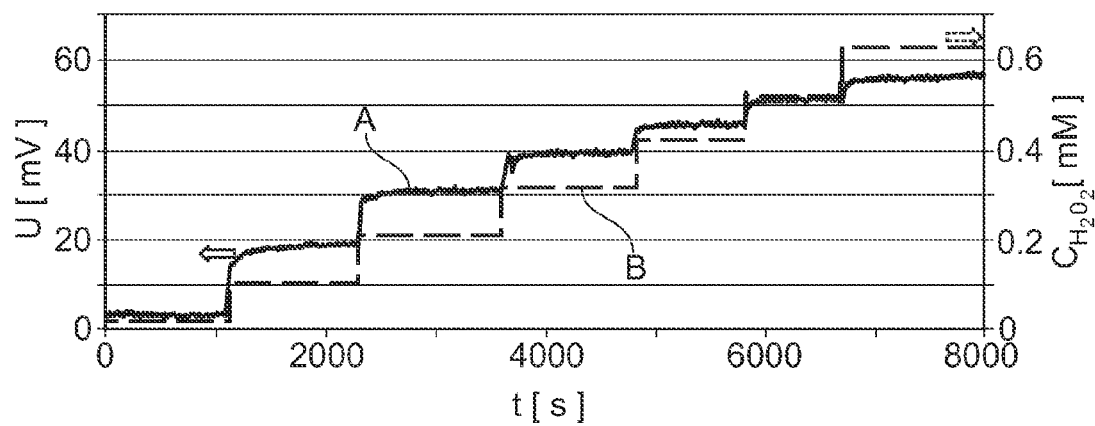
FIG. 3 shows an example of the graph of the voltage measured with the sensor in mV (left-hand axis) and of the hydrogen peroxide concentration in mmol (right-hand axis) over time.

FIG. 3 shows a measurement example of the voltage supplied by the sensor in millivolts along with the hydrogen peroxide concentration in millimoles over the time t in seconds. Therein, the left-hand ordinate indicates the voltage U in millivolts for the measurement curve A, and the right-hand ordinate indicates the hydrogen peroxide concentration in millimoles for the associated concentration graph which is represented by curve B. As can be seen, a new equilibrium voltage develops between the anode 1 and the cathode 2 across the load resistor 7 within a few seconds when the hydrogen peroxide concentration rises in a step-like manner.

Figure 4:
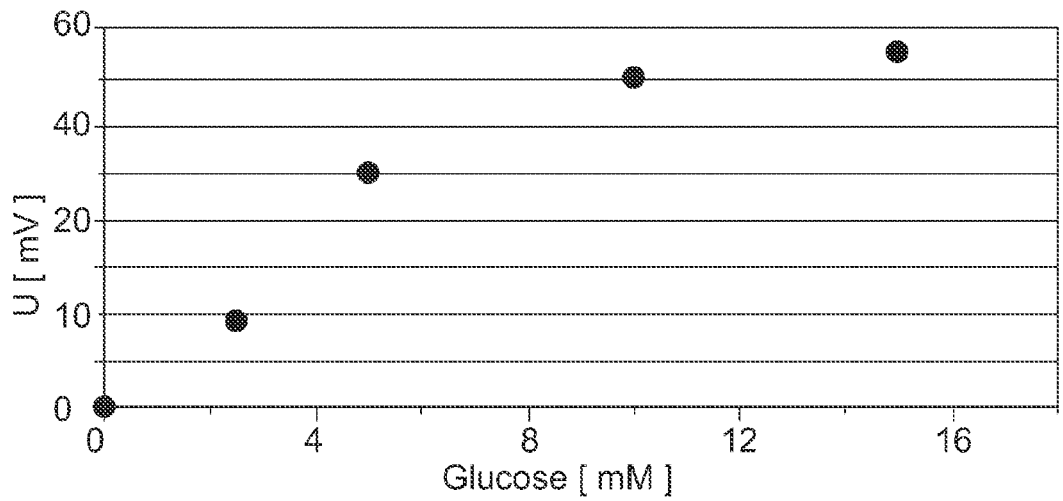
FIG. 4 shows a measurement example of the voltage delivered by the sensor in mV in relation to the glucose concentration in mmol.

FIG. 4 shows a measurement example of the voltage U supplied by the sensor in millivolts in relation to the glucose concentration in millimoles/liter. Therein, it can be seen that the electrical voltage between the anode and the cathode is higher as glucose concentration increases. For this reason, the associated glucose concentration can be determined with a calibration curve based on the measured voltage. An analyte concentration can, therefore, be determined by measuring the voltage dropping at a resistor 7 which connects a conductor 5 running to the anode to a conductor 6 running to the cathode.

Figure 5:
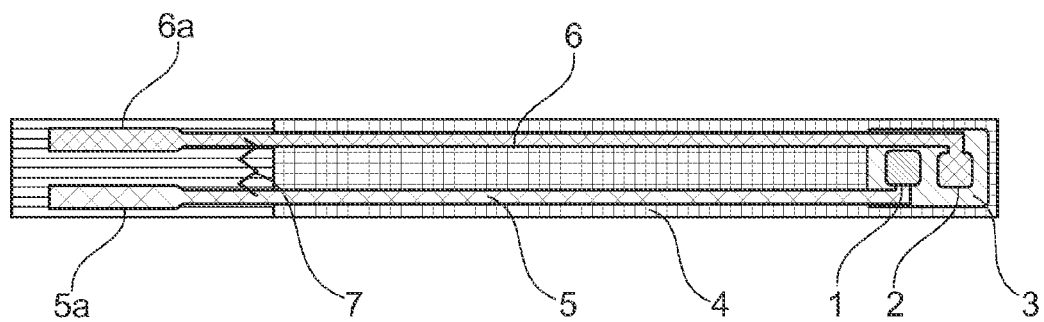
FIG. 5 shows a further embodiment of a sensor according to the invention.
Figure 6:
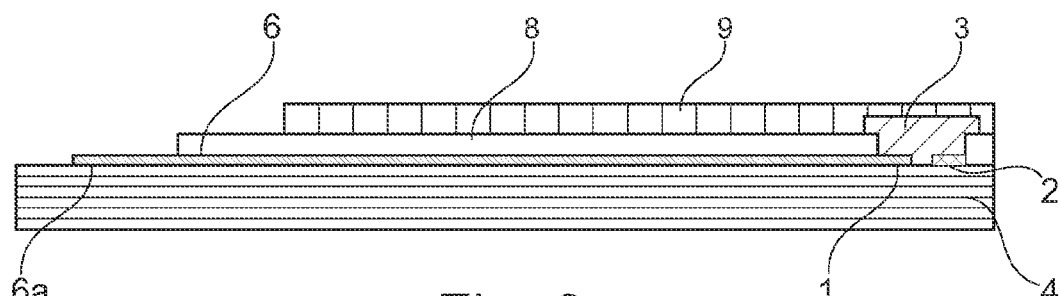
FIG. 6 is a sectional view of the sensor shown in FIG. 5.

FIG. 5 shows a further embodiment of a sensor according to the invention. FIG. 6 is a longitudinal sectional view of FIG. 5. In essence, the sensor shown in FIGS. 5 and 6 differs from the embodiment shown in FIGS. 1 and 2 only by a covering layer 9 covering the enzyme layer 3. The covering layer 9 is permeable to analyte molecules as well as water and can fulfill a plurality of functions which are each leading to an improvement of the sensor but are not necessarily required.

For example, the covering layer 9 can be impermeable to enzyme molecules. By counteracting an exit of enzyme molecules from the sensor, the compatibility of the sensor can be improved because exiting enzyme molecules might have harmful effects in the body tissue of a patient. This function of the covering layer 9 is, in particular, to advantage whenever the enzyme molecules in the enzyme layer 3 are not covalently bonded. The enzyme layer 3 can contain enzyme molecules that are covalently bonded. For example, enzyme molecules can be covalently bonded to polymers of a matrix. It is, however, also possible that the enzyme molecules are only admixed to the material of the enzyme layer 3 and can diffuse therein. Particularly in the latter case, a covering layer 9 that is impermeable to enzyme molecules is a significant advantage. For this purpose, the covering layer 9 can, for example, be produced from polyurethanes, polyvinyl chloride, polycarbonate, polytetrafluoroethylene, polyacrylates, silicones, polyvinyl pyrrole or mixtures of such polymers.

Advantageously, the covering layer 9 can also form a reservoir for analyte molecules. Analyte molecules can flow from said reservoir to the enzyme layer 3 in the event of a temporary failure of the fluid exchange in the environment of the sensor. If the exchange of body fluid is, temporarily, restricted or even prevented in the environment of the sensor, for example caused by movements of the patient's body, analyte molecules stored in the covering layer 9 can continue to diffuse to the enzyme layer 3. In this manner, the covering layer 9 can have the effect that a noticeable depletion of the analyte concentration and a corresponding falsification of the measurement results will not occur before a considerably longer time interval has elapsed. For this purpose, the covering layer 9 can also have a considerably greater thickness than is suggested in FIG. 6, which is not true to scale.

A further function of the covering layer 9 can be to provide a diffusion resistance for the analyte to be measured, i.e., act as a diffusion barrier. Due to its diffusion resistance, the covering layer 9 has the effect that a lesser number of analyte molecules arrive at the enzyme layer 3 per time unit. By means of the covering layer 9, the rate at which analyte molecules are converted can, therefore, be reduced and a depletion of an analyte concentration in the environment of the sensor, thus, be counteracted.

Figure 7:
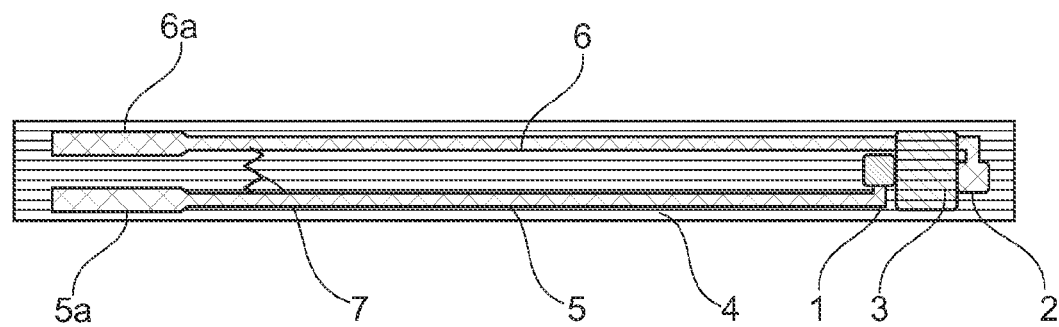
FIG. 7 shows a further embodiment of a sensor according to the invention.
Figure 8:
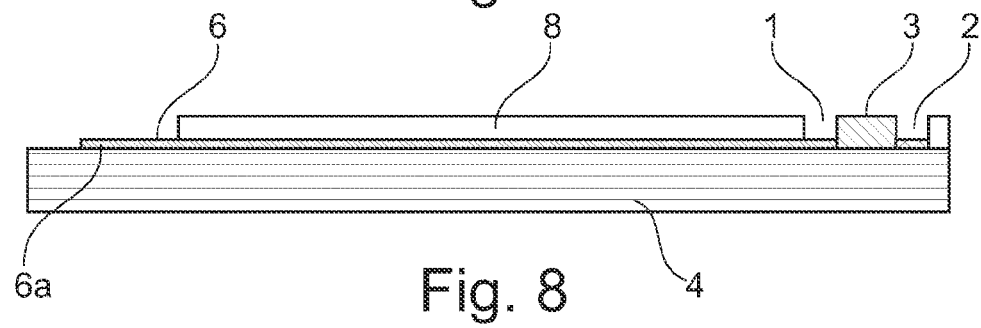
FIG. 8 is a longitudinal sectional view of a further embodiment of a sensor according to the invention.

A further embodiment of a sensor according to the invention is shown in FIG. 7. FIG. 8 is a longitudinal sectional view of FIG. 7. In essence, this embodiment differs from the embodiment of FIGS. 1 and 2 only in that the enzyme layer 3 does not cover the anode 1 and the cathode 2. Instead, the enzyme layer 3 is arranged between the anode 1 and the cathode 2. In this arrangement as well, the enzyme layer 3 forms a diffusion path for the analyte and the redox amphoteric product formed by the conversion thereof, for example hydrogen peroxide, to the anode 1 and to the cathode 2. As is the case in the remaining embodiments, the product is, therefore, oxidized on the anode 1 and reduced on the cathode 2.

The embodiment shown in FIGS. 7 and 8 can be provided with a covering layer 9, as has been illustrated above with respect to the embodiment shown in FIGS. 5 and 6. In the embodiments of FIGS. 7 and 8, a possible covering layer 9, preferably, does not only cover the enzyme layer 3 but also the anode 1 and the cathode 2.

Figure 9:
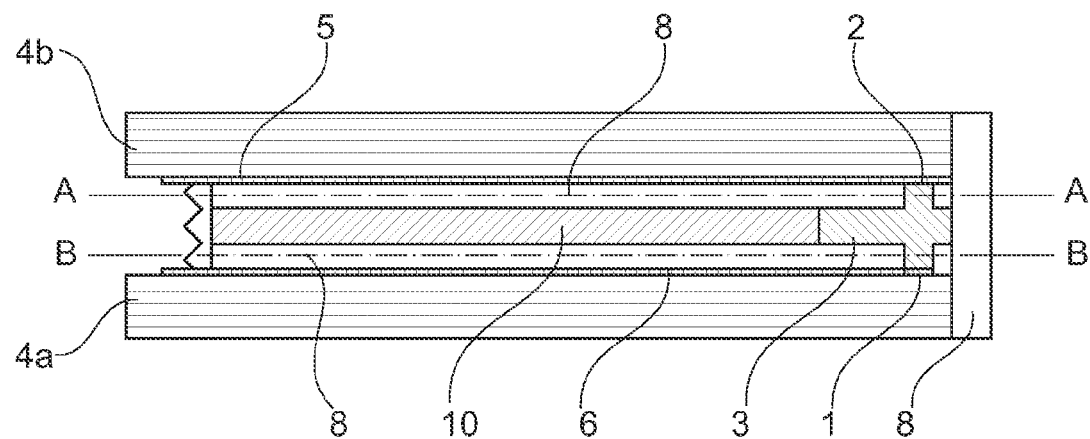
FIG. 9 is a longitudinal sectional view of a further embodiment of a sensor according to the invention.
Figure 10:
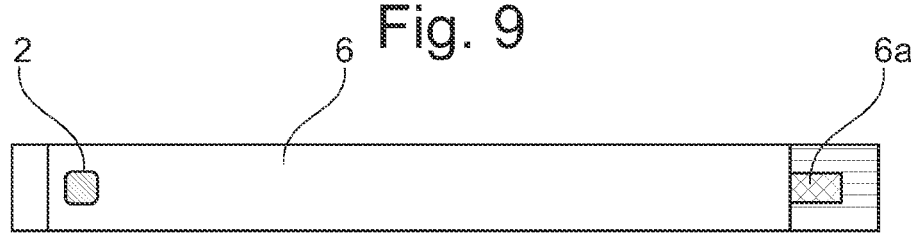
FIG. 10 is a sectional view taken from cutting line AA of FIG. 9.
Figure 11:
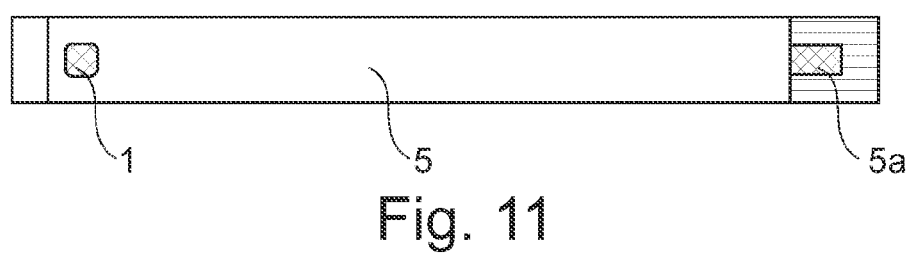
FIG. 11 is a sectional view taken from cutting line BB of FIG. 9.

FIG. 9 is a longitudinal sectional view of a further embodiment of a sensor according to the invention. FIG. 10 is a sectional view taken from cutting line AA of FIG. 9. FIG. 11 is a sectional view taken from cutting line BB of FIG. 9.

In this embodiment, the anode 1 and the cathode 2 are arranged on different substrates 4a, 4b. The substrates 4a, 4b can, for example, be formed as plastic sheets and each support a conducting track 5, 6, with the anode 1 and the cathode 2, respectively, being disposed at the ends of said conducting track 5, 6. The enzyme layer 3 is arranged between the two substrates 4a, 4b. The front face of this sandwiched arrangement is covered by a covering layer 9, such as it was illustrated in the context of the embodiment of FIGS. 5 and 6. As is the case with the embodiments described above, the conducting tracks 5, 6 can, likewise, be covered by an insulating layer 8. In addition, a spacer 10 can be arranged between the two substrates 4a, 4b.

In this embodiment, the load resistor 7 that connects the two conducting tracks 5, 6 can be a separate component that is arranged between the substrates 4a, 4b. For example, this component can be soldered to the conducting tracks 5, 6 or be connected thereto in a clamping manner. In particular, it is also possible that the spacer 10 supports the load resistor 7. For example, the resistor element 7 can be applied as a conducting paste into the intermediate space between the two substrates 4a, 4b and onto the front face of the spacer 10, with the result that the load resistor 7 comes into contact with the two conducting tracks 5, 6.

FIG. 12 is a longitudinal sectional view of a further exemplary embodiment of a sensor. FIG. 13 is a cross-sectional view of this sensor taken from cutting line AA plotted in FIG. 12. FIG. 14 is a cross-sectional view of this sensor taken from cutting line BB plotted in FIG. 12. FIG. 15 is a cross-sectional view of this sensor taken from cutting line CC plotted in FIG. 12.

In this embodiment, the anode 1 is arranged on the inner side of a sleeve and the cathode 2 is arranged on a conductor surrounded by the sleeve. This embodiment can be modified to the effect that the cathode 2 is arranged on the inner side of the sleeve and the anode is arranged on the conductor surrounded by the sleeve. For example, the conductor surrounded by the sleeve can be a wire. The sleeve can be made of metal or be a small plastic tube the inner side of which has a metallic coating in order to form an electrical conductor running to the electrode arranged on its inner side, preferably to the anode 1.

Similar to the embodiments described above, the conductors 5, 6 running to the anode 1 and the cathode 2 are covered with an insulating layer 8. The enzyme layer 3 is disposed between the anode 1 and the cathode 2. In the embodiment shown, the remaining interior region of the sensor is, in essence, completely filled with the enzyme layer 3, for example with a plastic matrix containing enzyme molecules. The front face of the sensor is covered with a covering layer 9, such as it can also be present in the embodiment illustrated above.

In the embodiment shown, the enzyme layer 3 extends to the load resistor 7 which connects the anode conductor to the cathode conductor. However, it can be to advantage to fill a section of the sleeve with insulating material. In this case, the load resistor 7 can be arranged spaced apart from the enzyme layer 3, for example on the insulating material closing the sleeve. In this embodiment as well, the load resistor 7 can be, advantageously, formed as a paste which contains carbon particles and solidifies after having been applied. It is, however, also possible to form the load resistor 7 as a conventional resistor element which is, for example, soldered to the anode conductor and the cathode conductor or is conductively connected thereto in any other manner.

FIG. 16 shows a further embodiment of an exemplary sensor. FIG. 17 is a sectional view of FIG. 16. In essence, this embodiment differs from the embodiment shown in FIGS. 5 and 6 only in that two anode-cathode pairs 1a, 2a and 1b, 2b are disposed therein. The conductor 6 is running to the anode 1*a*, the conductor 5 is running to the cathode 2*a*, the conductor 6*b* is running to the anode 1*b*, and the conductor 5*b* is running to the cathode 2*b*.

For this reason, the sensor shown has two fuel cells, with the result that, in principle, there are two different sensors. The two fuel cells can be provided for the measurement of the same analyte or, by using different enzymes, can be intended for the measurement of different analytes. For example, one of the two fuel cells can be provided for the measurement of glucose and the other fuel cell can be provided for the measurement of lactates. If both fuel cells are intended for the measurement of the same analyte, it is to particular advantage if the two fuel cells each form a sensor with different sensitivity. By measuring low analyte concentrations with one of the fuel cells and high analyte concentrations with the other fuel cell, it is possible to achieve a measurement precision that is higher as a whole. For example, different measurement sensitivities can be realized by different enzyme concentrations in the enzyme layers. A further possibility is to cover the enzyme layers with top layers 9 that are permeable to different degrees.

A further embodiment of a sensor is shown in FIG. 18. Similar to the embodiment shown in FIGS. 16 and 17, there are two different fuel cells in the sensor shown in FIG. 18 as well. In this embodiment, however, the two fuel cells are not arranged on the same side of a substrate. Instead, one of the two fuel cells is arranged on the top side and the other fuel cell on the bottom side of the substrate 4.

While exemplary embodiments incorporating the principles of the present invention have been disclosed hereinabove, the present invention is not limited to the disclosed embodiments. Instead, this application is intended to cover any variations, uses, or adaptations of the invention using its general principles. Further, this application is intended to cover such departures from the present disclosure as come within known or customary practice in the art to which this invention pertains and which fall within the limits of the appended claims.

REFERENCE SYMBOLS

1, 1*a*, 1*b* Anode
2, 2*a*, 2*b* Cathode
3 Enzyme layer
4 Substrate
5, 5*b* Conductor
5*a* Contact surface
6, 6*b* Conductor
6*a* Contact surface
7 Load resistor
8 Insulating layer
9 Covering layer
10 Spacer

What is claimed is:

1. A fuel cell, comprising:
    an anode and a cathode, the cathode having a surface made of a different material than that of the anode;
    an enzyme layer containing an enzyme for the catalytic conversion of a substance occurring in the human body, the enzyme layer forming a diffusion path to the anode and to the cathode for a fuel product generated by catalytic conversion of the substance, the fuel cell adapted to oxidize the fuel product on the anode and reduce it on the cathode; and
    wherein the substance for the catalytic conversion is an analyte to be measured and wherein the enzyme layer contacts the anode and the cathode.

2. The fuel cell of claim 1, wherein the anode and the cathode are arranged on a common substrate and the enzyme layer covers both the anode and the cathode.

3. The fuel cell of claim 1, wherein the cathode has a metallic surface.

4. The fuel cell of claim 1, wherein the anode has a non-metallic surface.

5. The fuel cell of claim 1, wherein the enzyme is an oxidase.

6. The a fuel cell of claim 1, wherein the fuel is hydrogen peroxide.

7. The fuel cell of claim 1, wherein the enzyme layer is an insulator in its dry state.

8. The fuel cell of claim 1, wherein an electrical resistor connects a first conductor running to the anode to a second conductor running to the cathode.

9. The fuel cell of claim 8, wherein the resistor is a mixture which contains carbon particles and a binding agent.

10. The fuel cell of claim 1, wherein the enzyme layer is covered by a covering layer.

* * * * *